United States Patent [19]
Topel et al.

[11] Patent Number: 5,488,958
[45] Date of Patent: Feb. 6, 1996

[54] SURGICAL CUTTING INSTRUMENT FOR CORING TISSUE AFFIXED THERETO

[75] Inventors: Howard C. Topel, Deerfield, Ill.; Thomas L. Foster, Poland, Ind.

[73] Assignee: Vance Products Incorporated, Spencer, Ind.

[21] Appl. No.: 335,221

[22] Filed: Nov. 7, 1994

Related U.S. Application Data

[63] Continuation of Ser. No. 973,847, Nov. 9, 1992, abandoned.

[51] Int. Cl.⁶ .................................................. A61B 17/32
[52] U.S. Cl. ........................... 128/754; 606/180; 606/184
[58] Field of Search .................................... 606/180, 184; 128/754, 751; 30/361, 113.1, 113.2

[56] References Cited

U.S. PATENT DOCUMENTS

| | | | |
|---|---|---|---|
| 1,888,347 | 11/1932 | Diamond | 30/361 |
| 2,850,007 | 9/1958 | Lingley | 128/754 |
| 3,995,619 | 12/1976 | Glatzer | 128/2 B |
| 4,010,543 | 3/1977 | Nusbaum | 30/113.1 |
| 4,010,737 | 3/1977 | Vilaghy et al. | 128/754 |
| 4,682,606 | 7/1987 | DeCaprio | 128/754 |
| 5,018,530 | 5/1991 | Rank et al. | 128/754 |

FOREIGN PATENT DOCUMENTS 9212676  8/1992  WIPO.

OTHER PUBLICATIONS

Semm, K., "Pelviscopy–Operative Guidelines," 1988.
Nordenström, Björn, "New Instruments for Biopsy", Radiology, vol. 117, pp. 474–475, Nov. 1975.

*Primary Examiner*—Tamara L. Graysay
*Attorney, Agent, or Firm*—Richard J. Godlewski

[57] ABSTRACT

A surgical cutting instrument for coring, debulking, and removing a large, tough tissue mass such as a fibroid tumor through a trocar access sheath during a minimally invasive surgical procedure. The instrument includes an outer sheath having a distal cutting end for coring the tissue mass and an inner elongated member having a distal, tissue affixation end such as a helical coil for inserting into and stabilizing the tissue mass during the surgical coring procedure. The cutting instrument further includes an instrument engagement assembly when in an engaged position for urging the outer sheath toward the distal end of the inner elongated member. As a result, tissue affixed to the distal end of the inner elongated member is cored as the outer sheath is urged toward the distal end of the inner member and engages the affixed tissue. The instrument engagement assembly includes sheath and member engagement subassemblies. The sheath engagement subassembly is positioned about the proximal end of the outer sheath and includes a hub with a pivotedly interconnected side arm. The member engagement subassembly positioned along the intermediate portion of the inner member includes multiple start helical threads. The side arm has projections extending laterally therefrom for extension into the passage of the hub and engaging the multiple start helical threads of the inner member.

5 Claims, 7 Drawing Sheets

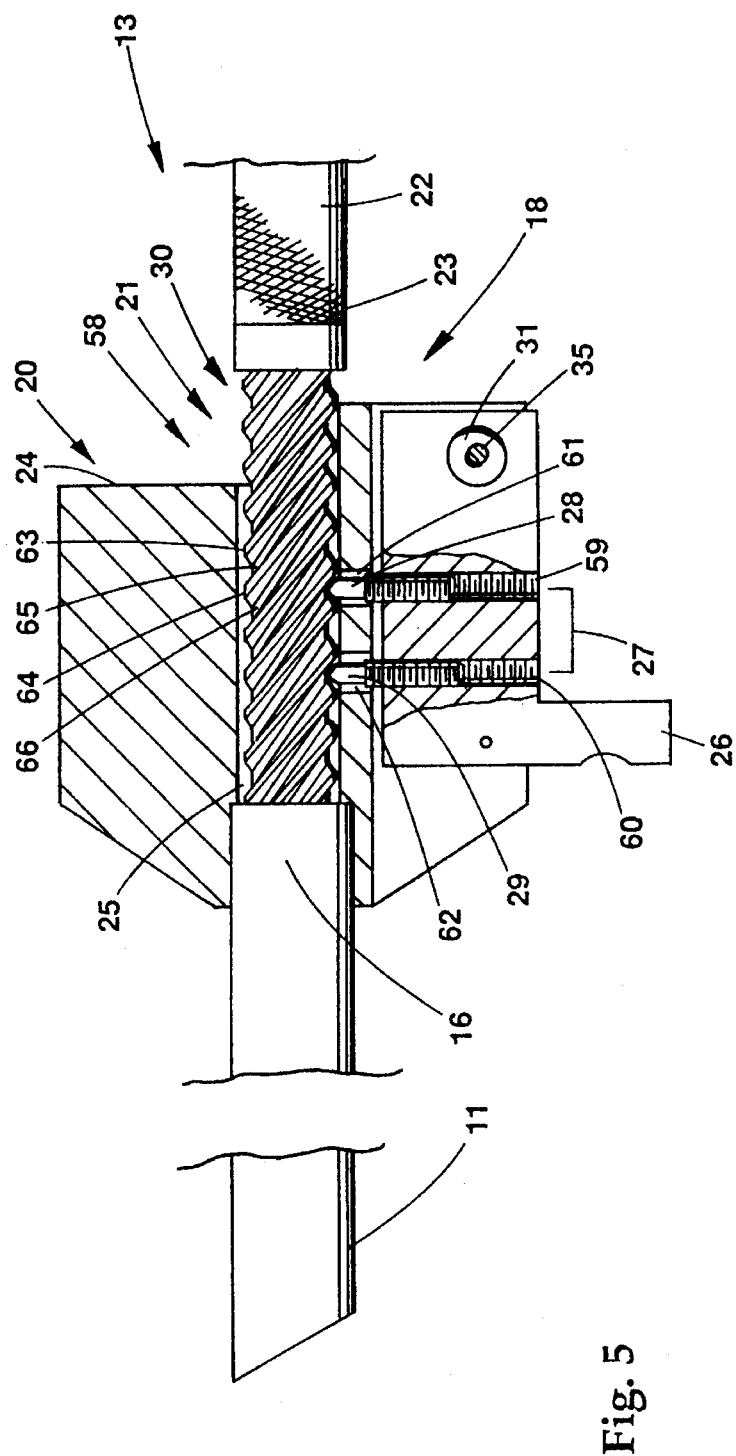
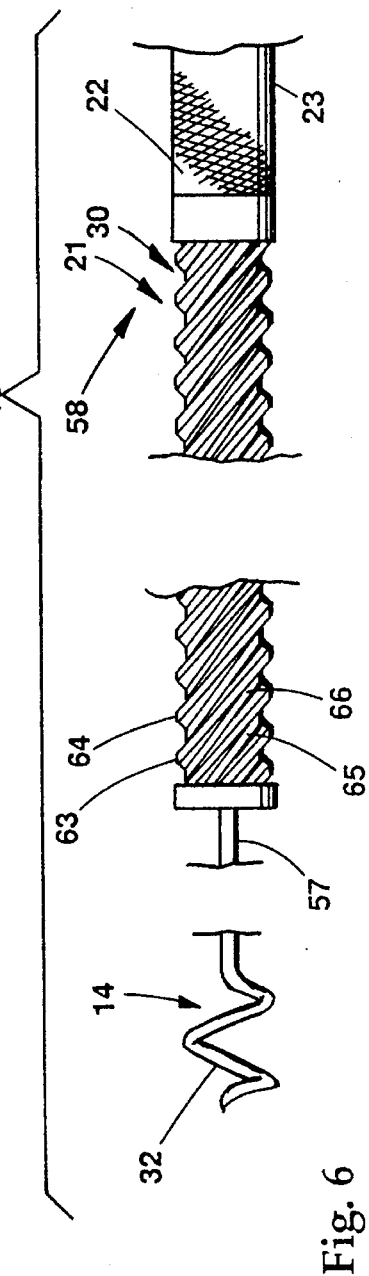
Fig. 5
Fig. 6

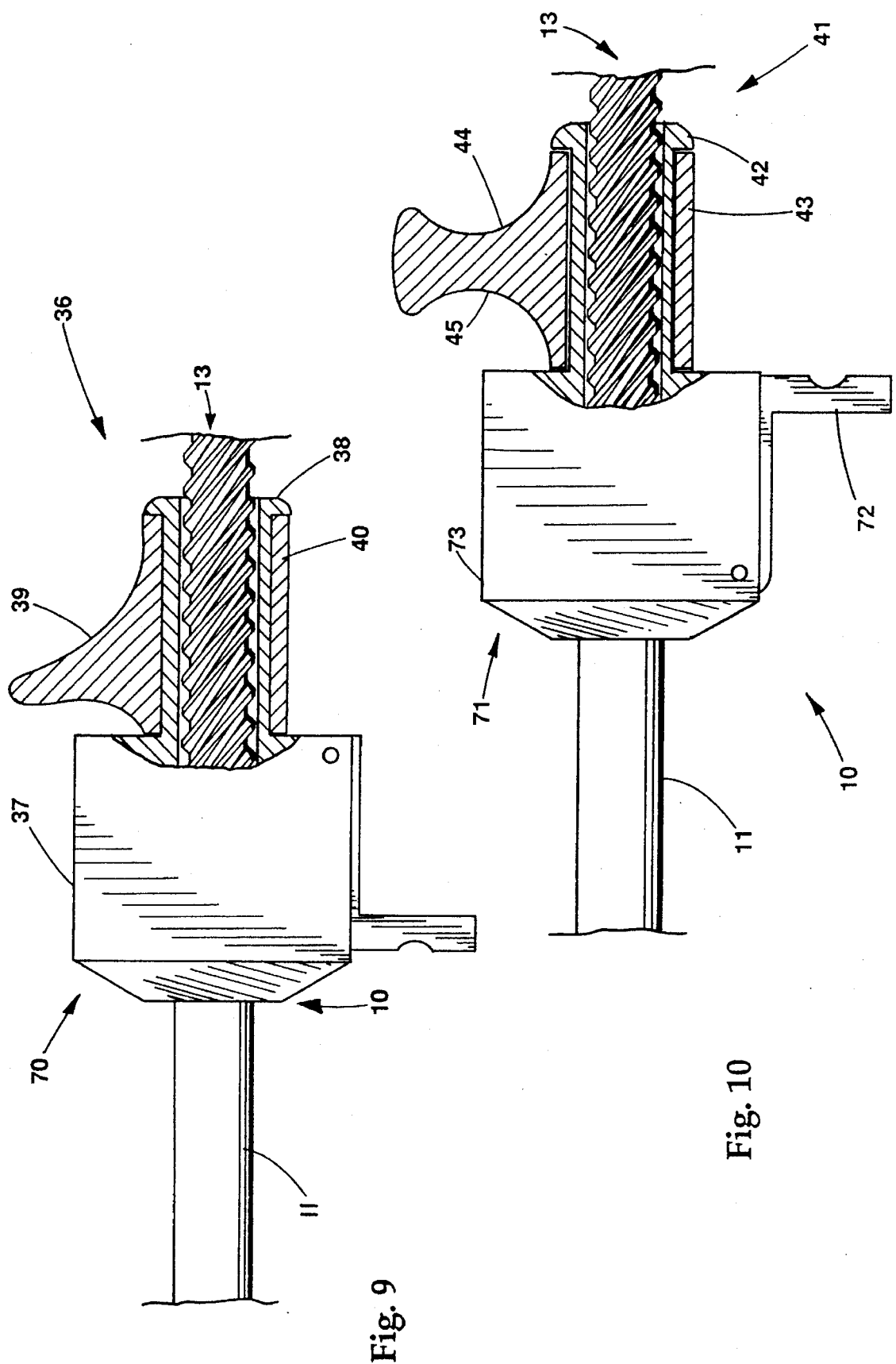

SURGICAL CUTTING INSTRUMENT FOR CORING TISSUE AFFIXED THERETO

This is a continuation of application Ser. No. 07/973,847 filed on Nov. 9, 1992, now abandoned.

TECHNICAL FIELD

This invention relates generally to surgical cutting instruments and particularly to surgical cutting instruments for use in minimally invasive, surgical procedures to morcellate fibroid tumors.

BACKGROUND OF THE INVENTION

Undesirable tissue masses such as fibroid tumors are typically dense, tough, and bulky. These characteristics make it difficult to remove a relatively dense tumor using the instruments typically used in minimally invasive endoscopic surgery. Endoscopic tissue graspers and cutters have jaws of limited size and inadequate closing force. Therefore, fibroid tumors are commonly removed by open surgery, which permits direct manipulation and cutting. As a result of the open surgical procedure, the patient experiences a long hospital stay and a long healing and recovery period of six to eight weeks along with a greater risk of infection and a larger area of scarring.

One approach to endoscopically grasping a tumor is through the use of a myoma drill. This drill comprises a rod with a helically shaped distal end for rotatably advancing into the tumor tissue. When positioned in the tumor tissue, the helical drill is used for only manipulating the tissue. A limitation of the drill is that it is only useful as a manipulator. A separate surgical instrument is necessary for cutting the tumor tissue.

One approach to endoscopically removing tissue is through the use of a surgical instrument including a hollow inner tube with a crochet-type hook at the distal end thereof. The instrument also includes an outside cutting sleeve with a rotary cutting edge. The rotary cutting edge turns about the axis of the hollow tube to sweep a portion of the crochet-hook face, thereby cutting an object, such as a suture thread or tissue, that is positioned about the hook for removing sutures and biopsy samples. A problem with this instrument is that the outside cutting sleeve can cut only a small object. The instrument cannot cut a relatively large portion of tissue or systematically debulk a tissue mass such as a fibroid tumor. Furthermore, the crochet-hook of the instrument cannot grasp or stabilize a tumor or a relatively large portion of tissue.

Another approach to endoscopically removing tissue is through the use of a biopsy apparatus including an inner cylinder with a distally positioned corkscrew and an outer barrel with a distally positioned pair of cutting jaws for removing tissue masses such as lesions that are too small to be palpable. When the corkscrew is positioned in tissue, the outer barrel is advanced thereover and the jaws are actuated closed for cutting small bites of soft or fatty tissue. A problem with this apparatus is that the cutting jaws close with an inadequate amount of force. As a result, the apparatus cannot cut tough or fibrous tissue. Furthermore, the action of the jaws serves to push tissue distally away from the jaws so that most of the tissue recedes and only a small bite is cut out of the tissue mass. As a result, the apparatus does not penetrate tissue for debulking a large or dense tumor.

SUMMARY OF THE INVENTION

The foregoing problems are solved and a technical advance is achieved in an illustrative endoscopic surgical cutting instrument for coring, debulking, and removing large, tough tissue masses such as a fibroid tumor affixed to the distal end thereof. The instrument includes an outer sheath having a distal cutting end and a hollow passage extending longitudinally therethrough. The instrument also includes an inner elongated member sized for insertion through the passage of the outer sheath. The inner elongated member has a distal, tissue affixation end that is extendable from the distal cutting end of the outer sheath and positionable in the tissue for advantageously stabilizing the tissue during the surgical coring procedure. The cutting instrument includes an instrument engagement assembly when in an engaged position for urging the outer sheath toward the distal end of the inner elongated member. As a result, a large, tough tissue mass affixed to the distal end of the inner elongated member is advantageously cored as the outer sheath is urged toward the distal end of the elongated member and engages the affixed tissue. The cutting instrument is insertable through a trocar access sheath during a minimally invasive surgical procedure for advantageously coring, debulking, and removing a large fibroid tumor through the access sheath without the need for a large traumatic incision in the patient. This significantly reduces the patient's length of stay in the hospital and the recovery period associated with the surgery. Scarring is minimized along with the possibility of lesions and adhesions in the internal cavity of the patient.

The instrument engagement assembly includes a sheath engagement subassembly positioned on the outer sheath and a member engagement subassembly positioned on the elongated member for selectively engaging each other. The instrument engagement assembly in a disengaged or released position advantageously provides for the insertion and removal of the inner elongated member along with cored tissue.

The sheath engagement subassembly includes a hub attached about the proximal end of the outer sheath and has a passage communicating with the passage of the outer sheath for inserting the inner elongated member therethrough.

The member engagement subassembly includes an intermediate portion with multiple start helical threads along the outer surface thereof. The hub of the sheath engagement subassembly includes selector means such as a side arm pivotedly connected to the hub. The side arm has at least one projection extending laterally therefrom and into the passage of the hub for engaging the multiple start helical threads of the inner elongated member when the instrument engagement assembly is in the engaged position. The multiple start helical threads and side arm projections extending therein engage each other to urge the outer sheath toward the distal end of the elongated member as the surgeon rotates the outer sheath around the inner member.

In an another embodiment of the present invention the selector means comprises an arm slidably attached to the proximal end of the hub. The slide arm has a slot positioned therethrough communicating with the passage of the hub. The slot has a plurality of at least partial helical grooves for mating with the helical threads of the elongated member when the instrument engagement assembly is in the engaged position.

In still another embodiment of the present invention, the hub includes an inner sleeve extending proximally therefrom. An outer sleeve is fixedly positioned longitudinally about the inner sleeve and is rotatable thereabout. The outer sleeve includes a thumb rest positioned on the outer surface of the outer sleeve, thereby providing the physician with additional comfort in rotating the outer sleeve during the surgical coring procedure.

In yet another embodiment of the present invention, the outer sleeve of the sheath engagement subassembly also includes a finger pull for removing the outer sheath as it rotates about the engaged inner elongated member.

To advantageously enhance the cutting action of the instrument, the distal cutting end of the outer sheath includes a cutting edge positioned circumferentially thereabout. The distal cutting edge is beveled with respect to the longitudinal axis of the outer sheath to further enhance the cutting action of the instrument.

The distal, tissue affixation end of the inner elongated member includes a helical coil in the form of a corkscrew for advantageously inserting the inner elongated member into the tough fibroid tumor and stabilizing the tumor during the surgical coring procedure.

BRIEF DESCRIPTION OF THE DRAWING

FIG. 5 depicts a partially sectioned view of the instrument engagement assembly of the instrument of FIG. 1 in an engaged position;

FIG. 6 depicts a partial view of the elongated member of the instrument of FIG. 1;

FIG. 9 depicts still another embodiment of the present invention including a second alternative instrument engagement assembly for the instrument of FIG. 1; and FIG. 10 depicts yet another embodiment of the present invention including an enhancement to the instrument engagement assembly for the instrument of FIG. 9.

DETAILED DESCRIPTION

Figure 1:
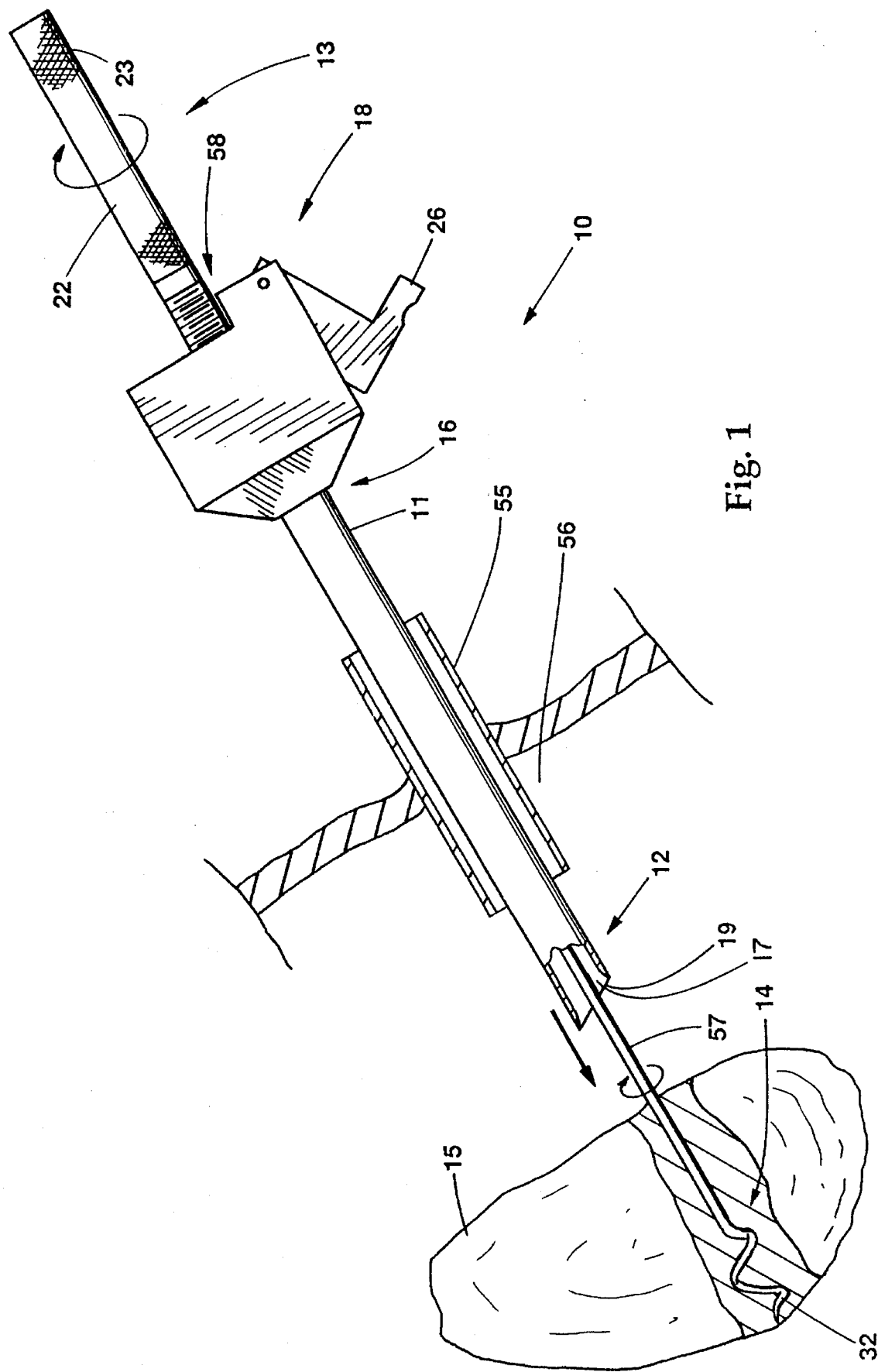
FIG. 1 depicts a preferred surgical cutting instrument of the present invention extending into the body cavity of a patient through a surgical access sheath.

FIG. 1 depicts preferred surgical cutting instrument 10 positioned through a commercially available, trocar access sheath 55 for morcellating fibroid tumor 15 in body cavity 56 of a patient during a minimally invasive surgical procedure. The instrument includes outer sheath 11 and inner elongated member 13. The outer sheath includes distal cutting end 12 with circumferential cutting edge 19, proximal end 16 and passage 17 extending longitudinally therebetween for positioning elongated member 13 therethrough. Elongated member 13 is sized for insertion through passage 17 and includes distal rod 57 with distal, tissue affixation end 14 that is extendable from the distal cutting end of the outer sheath when the member is positioned in the passage of the sheath. As depicted, distal tissue affixation end comprises helical coil 32. The elongated member also includes proximal handle 23 with knurled outer surface 22 and intermediate portion 58. Outer sheath 11 and inner elongated member 13 are longitudinally movable with respect to each other via instrument engagement assembly 18, which is depicted with side arm 26 in a disengaged or released position. The instrument engagement assembly with side arm 26 in an engaged position urges the outer sheath toward the distal end of the elongated member as the outer sheath is rotated in a clockwise direction. As a result, tissue affixed to the distal end of the elongated member is cored as the distal cutting end of the outer sheath engages and cuts the affixed tissue.

During a minimally invasive surgical procedure, distal end 14 of elongated member 13 is drawn into passage 17 of the outer sheath for introducing instrument 10 into body cavity 56 of the patient through trocar access sheath 55. When the instrument is positioned in the body cavity, helical coil 32 is extended from distal cutting end 12 of outer sheath 11 and rotatably advanced into fibroid tumor 15 for stabilizing the position of the tumor with respect to the distal cutting end of the outer sheath.

Figure 2:
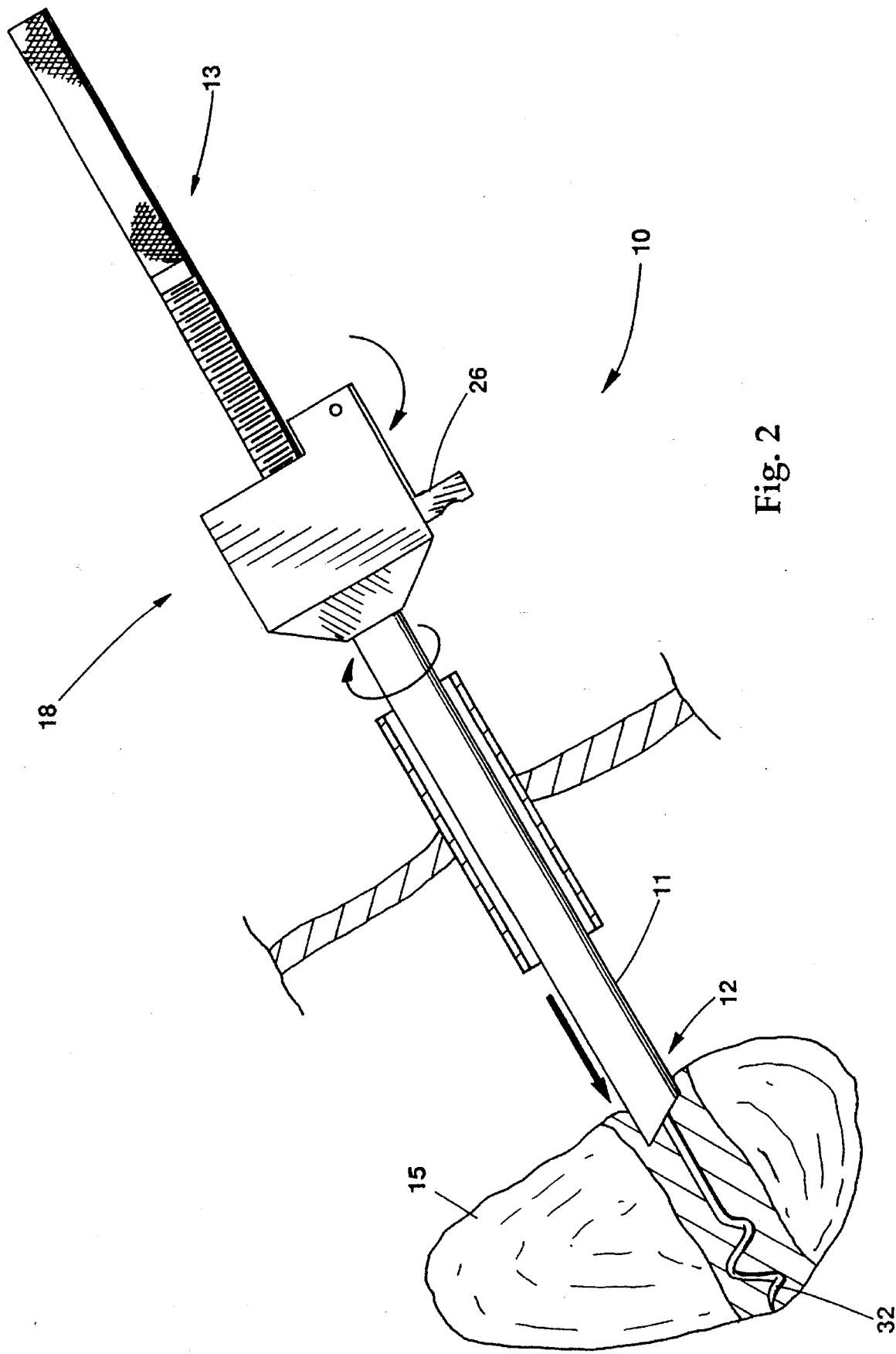
FIG. 2 depicts a partially sectioned view of the instrument of FIG. 1 engaging and cutting into fibroid tumor tissue.

FIG. 2 depicts a partially sectioned view of surgical cutting instrument 10 with helical coil 32 of the elongated member positioned in fibroid tumor tissue 15 and distal cutting end 12 of outer sheath 11 initially engaging and cutting into the fibroid tumor tissue. Side arm 26 of instrument engagement assembly 18 is in the engaged position. Outer sheath 11 is being rotated and urged toward helical coil 32 of elongated member 13 so that distal cutting end 12 engages and initially cuts into the fibroid tumor tissue.

Figure 3:
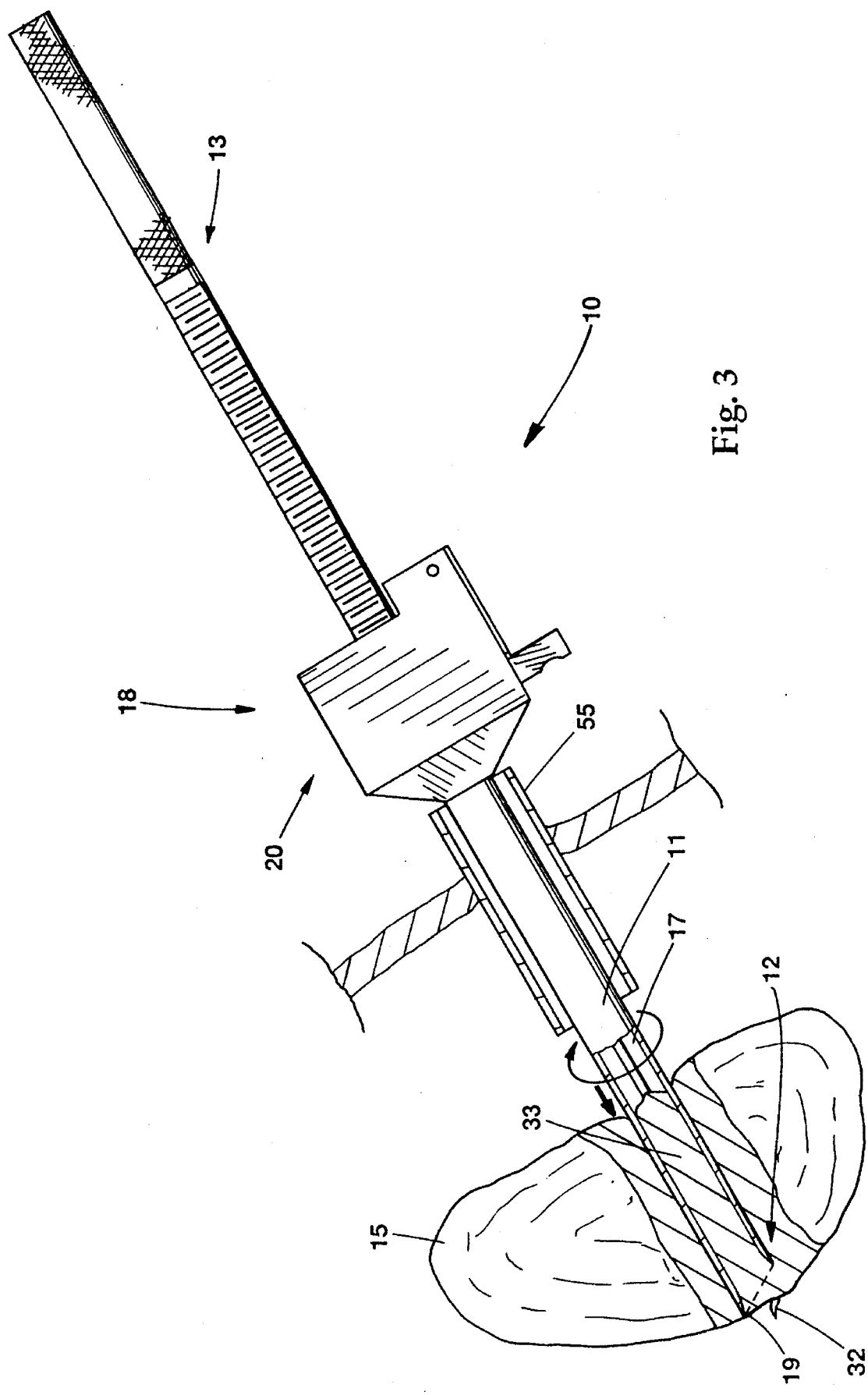
FIG. 3 depicts a partially sectioned view of the instrument of FIG. 1 coring a plug of the fibroid tumor tissue.
Figure 4:
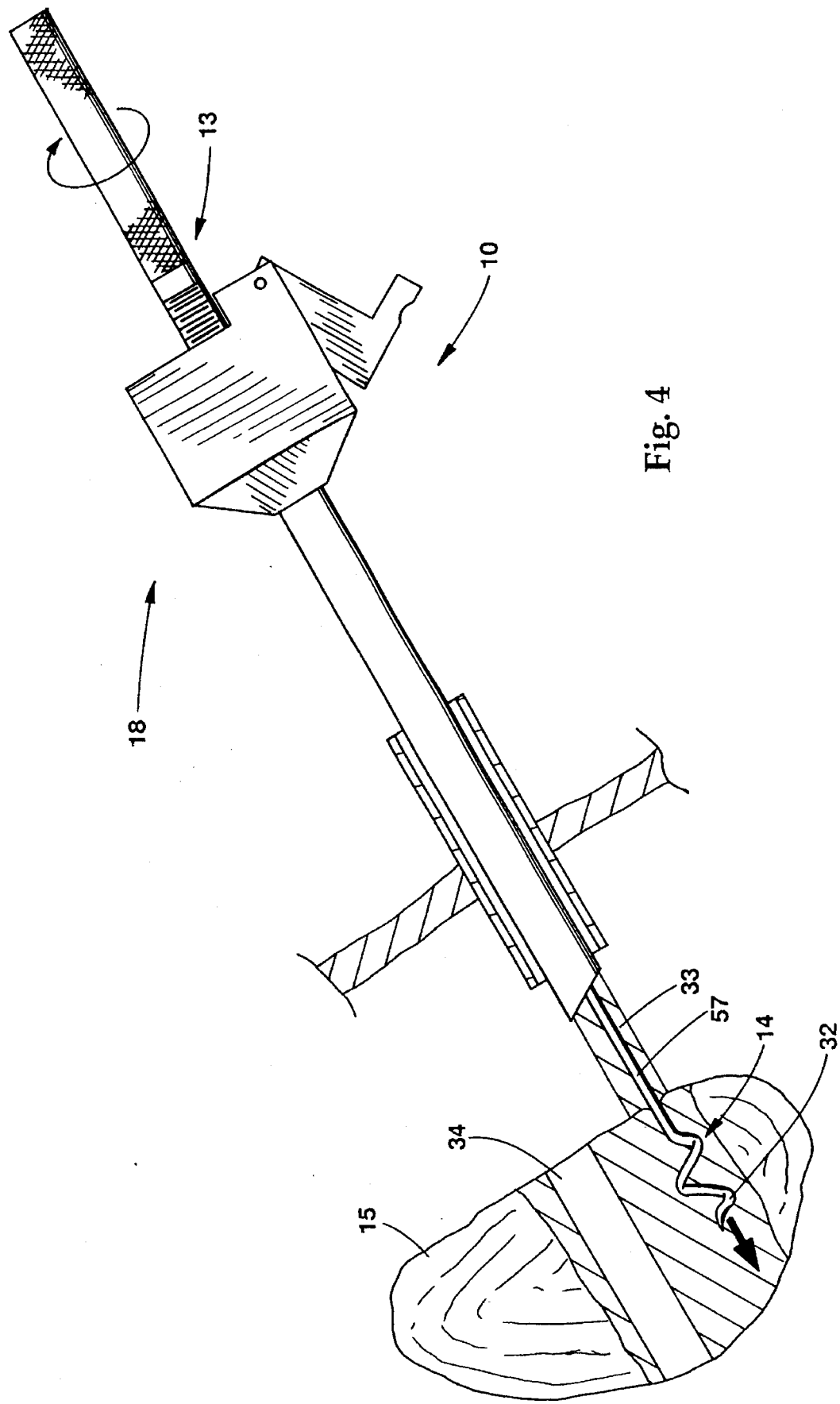
FIG. 4 depicts a partially sectioned longitudinal view of the instrument of FIG. 1 with the distal, tissue affixation end being repositioned in the fibroid tumor tissue.

FIG. 3 depicts a partially sectioned view of surgical cutting instrument 10 further cutting and coring into fibroid tumor tissue 15 with helical coil 32 positioned in and stabilizing the tissue. Outer sheath 11 is rotatably advanced toward the distal end of helical coil 32 to cut cylindrically shaped plug 33 of fibroid tumor tissue 15 with the helical coil securely positioned therein. When cutting edge 19 of distal cutting end 12 and the outer sheath are advanced distally, the cylindrically shaped plug of tissue is positioned in passage 17 of the outer sheath. Cutting edge 19 of distal cutting edge 12 is formed at an angle of approximately 30° with respect to the longitudinal axis of outer sheath 11 to improve the cutting action. Cutting edge 19 can also include serrations and be alternatively positioned transverse to the axis of outer sheath 11. Instrument 10 is then pulled proximally and removed from the tissue, leaving tissue passage 34, as depicted in FIG. 4. The helical coil of the elongated member is repositioned for engaging another portion of the fibroid tumor tissue. Decreasing the bulk of a fibroid tumor tissue mass by coring or removing one cylindrically shaped plug of tissue at a time through the small opening of trocar access sheath 55 with, for example, a 5 to 10 mm diameter, allows for the removal of a relatively large mass of tissue from the body of the patient without a large, traumatic surgical incision.

FIG. 4 depicts a partially sectioned view of surgical cutting instrument 10 removed from tissue passage 34 and repositioned in fibroid tumor tissue 15 for removing another cylindrically shaped tissue plug. When so repositioned, helical coil 32 is again advanced into tissue 15. As the helical coil is advanced distally, cylindrically shaped tissue plug 33 contacts tissue 15 for pushing cylindrically shaped tissue plug 33 proximally along distal rod 57 of elongated member 13. Then the outer sheath is rotatably advanced distally toward the helical coil to engage and cut another cylindrically shaped plug of tissue 15. Additional cylindrically shaped tissue plugs are cut and pushed proximally along the elongated member until the outer sheath is filled with tissue plugs. The plugs of tissue are conveniently removed from the elongated member after removal from the passage of the outer sheath by first releasing or disengaging instrument engagement assembly 18 of the instrument and removing the elongated member from the passage of the outer sheath while leaving the outer sheath positioned in the body cavity of the patient. The cleaned elongated member is replaced in the passage of the outer sheath, and the instrument engagement assembly is placed in the engaged position for removing additional cylindrically shaped plugs of tissue until the tumor tissue is completely morcellated or debulked. Alternatively, the instrument is removed from the body cavity before releasing or disengaging the instrument engagement assembly of the instrument and removing the elongated member from the passage of the outer sheath.

FIG. 5 depicts a partially sectioned side view of instrument engagement assembly 18 in the engaged position for providing forcible, rotational and longitudinal movement of outer sheath 11 and inner elongated member 13 with respect to each other. Engagement assembly 18 includes sheath engagement subassembly 20, which is positioned about proximal end 16 of outer sheath 11, and member engagement subassembly 21, which is positioned along intermediate portion 58 of member 13, for selectively engaging each other. Sheath engagement subassembly 20 includes hub 24 with passage 25 extending longitudinally therethrough and communicating with the passage of outer sheath 11 for positioning member engagement subassembly 21 of elongated member 13 therein. Sheath engagement subassembly 20 further includes side arm 26 that is pivotedly connected to hub 24, as depicted, with pivot pin 35 for moving between the released and engaged positions. Commercially available rubber O-rings 31 are positioned around the pivot pin between the side arm and hub for frictionally maintaining the side arm in a selected position with respect to the hub. Side arm 26 of the sheath engagement subassembly includes selector portion 27 with projections 28 and 29 threadably and adjustably positioned in respective apertures 59 and 60 extending laterally through the side arm. Projections 28 and 29 extend laterally from side arm 26 and through respective hub apertures 61 and 62 and into respective helical grooves 65 and 66 for engaging respective multiple-start threads 63 and 64 of member engagement subassembly 21 when the side arm is in the depicted engaged position. Member engagement subassembly 21 includes positioning apparatus 30 with multiple-start helical threads 63 and 64 and helical grooves 65 and 66 positioned in the outer surface of intermediate portion 58 of elongated member 13. In the released position, side arm 26 of instrument engagement assembly 18 is pulled upward for disengaging projections 28 and 29 and from helical threads 63 and 64 and helical grooves 65 and 66. In the released position, the elongated member is easily pulled proximally from the passage of the outer sheath.

FIG. 6 depicts a partial view of elongated member 13 with member engagement subassembly 21 positioned along intermediate member portion 58. Member engagement subassembly 21 includes positioning apparatus 30 with multiple-start helical threads 63 and 64 and helical grooves 65 and 66 for engaging projections 28 and 29 when the instrument engagement assembly of surgical cutting instrument 10 is in the engaged position. When in the engaged position, projections 28 and 29 remain in contact with multiple-start threads 63 and 64. Multiple-start threads 63 and 64 include, for example, two or three, and preferably five, starts of external threads. Multiple starts or sets of external threads provide for more forcible, rapid advancement of the elongated member while minimizing muscle fatigue of a surgeon during repeated rotation of the instrument.

As depicted in FIGS. 5 and 6, distal rod 57 of inner elongated member 13 comprises, for example, 300 series stainless steel approximately 8" long with a 0.090" diameter. Helical coil 32 of distal, tissue affixation end 14 is approximately 0.875" long with a 0.190" outside diameter. Distal rod 57 is soldered, using silver solder and an end cap, to the distal end of member engagement subassembly 21. The subassembly comprises a 6" long, ⅜-16 stainless steel, externally threaded rod having five start, 1.200 per inch threads. The threaded rod of the member engagement subassembly is buffed to remove sharp points and has a maximum major diameter of approximately 0.360". The threaded rod is soldered, using silver solder and an end cap, to proximal handle 23 of the elongated member. The handle comprises a stainless steel rod approximately 2.500" long and 0.375" in diameter with knurled outer surface 22 for enhancing the grip of the surgeon. The solder joints are strengthened by positioning a 0.250" length of the smaller member in a hole drilled about the center line of the larger member.

Outer sheath 11 comprises a series 304 stainless steel tube approximately 11" long with a 0.428" outside diameter and a 0.010" wall thickness. The outer sheath tube is fixedly attached to hub 24 of the sheath engagement subassembly 20 by commercially available, medical grade adhesive. Hub 24 comprises a clear polycarbonate material approximately 1.500" long, 1.250" wide, and 0.750" high. The corners at the distal end of the hub have a 45 degree bevel extending proximally longitudinally 0.375". A groove approximately 0.380" wide and 0.375" deep extends longitudinally approximately 1.250" for positioning side arm 26 therein. A portion of the proximal end of the hub material is removed at a depth of 0.250" for a length of 0.725". Passage 25 of the hub has an approximately 0.428" diameter. Side arm 26 of the sheath engagement subassembly comprises a clear polycarbonate material approximately 1.500" long, 0.875" wide, and 0.375" deep. The arm is formed by removing a 1.125" length and 0.500" wide portion of material and beveling the distal and proximal outside corners of the arm. Apertures 59 and 60 are drilled and threaded through the arm approximately 0.500" from the pivotal end of the arm and spaced with the center lines of the holes approximately 0.250" apart using a standard 8–32 drill bit. Pins such as standard 8–32 set screws are threaded and glued into the drilled holes for forming projections 28 and 29. The pins have an outside diameter of ¹⁄₁₆" and extend from the arm approximately 0.100" for being positioned in positioning portion 27 of outer sheath engagement subassembly 20. Alternatively, hub 24 and side arm 26 are injection molded with integrally formed beveled surface, passages, and projections 28 and 29.

Figure 7:
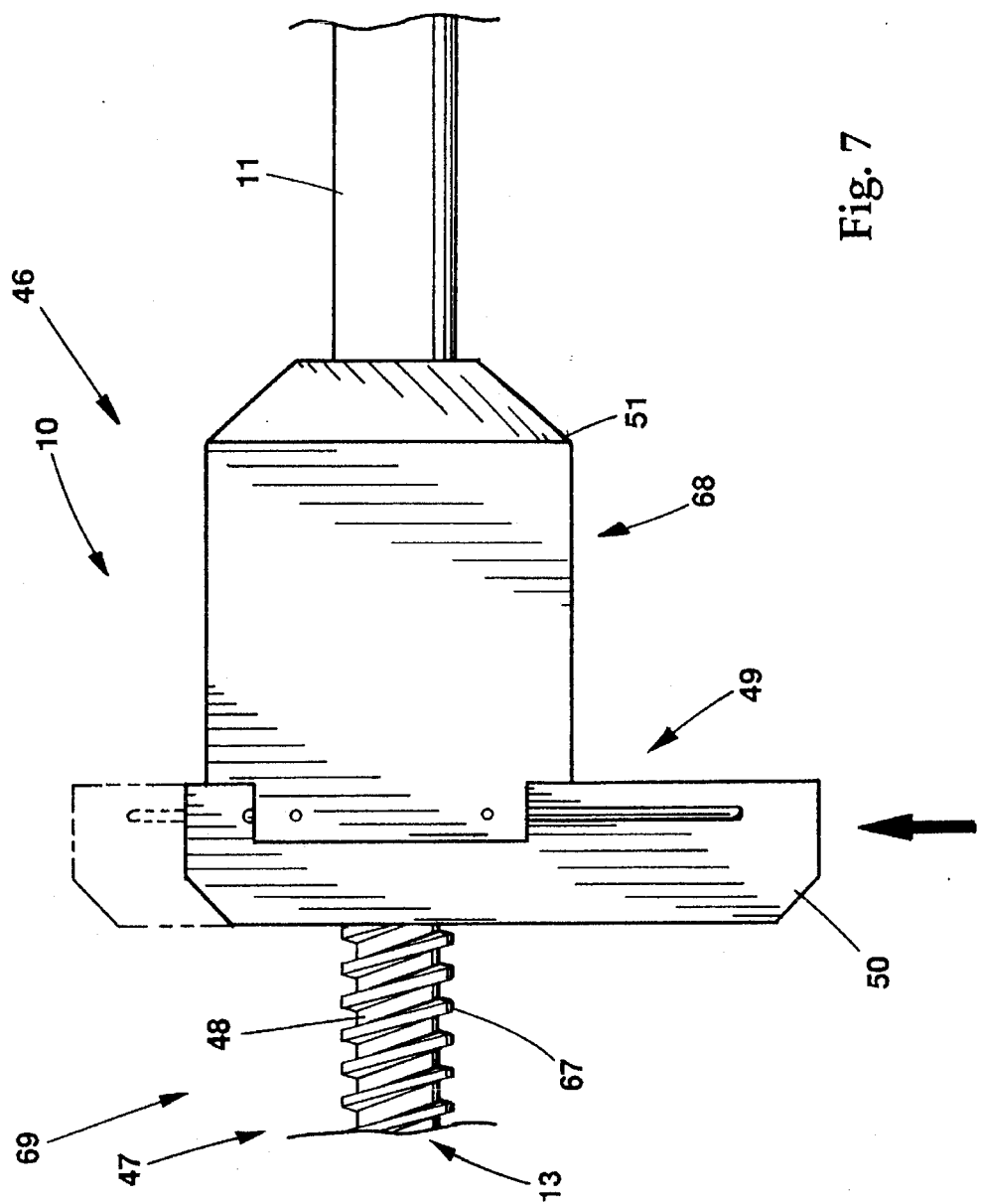
FIGS. 7 and 8 depict another embodiment of the present invention including an alternative instrument engagement assembly for the instrument of FIG. 1.
Figure 8:
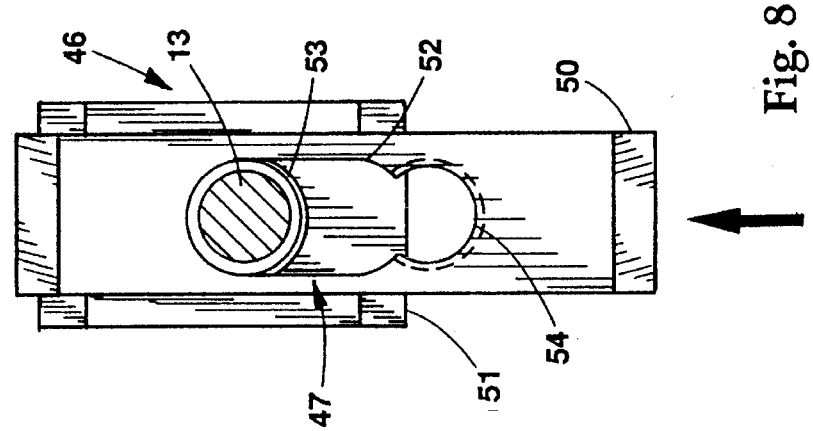

FIGS. 7 and 8 depict another embodiment of the present invention including alternative instrument engagement assembly 46 for instrument 10 including sheath engagement subassembly 68 positioned on outer sheath 11 and member engagement subassembly 69 positioned on inner elongated member 13. The member subassembly includes intermediate positioning portion 47, helical groove 48 and one-start helical external thread 67 formed in the outer surface thereof. Sheath engagement subassembly 68 includes selector apparatus 49 with slide arm 50 slidably attached to hub 51. Slide arm 50 has slot 52 extending therethrough and communicating with passage 53 of the hub. Slot 52 includes a plurality 54 of partial grooves or internal threads positioned along one side thereof for mating with helical groove 48 and thread 67. When slide arm 50 is slid laterally to the engaged position for mating the positioning portion of the elongated member with plurality 54 of partial grooves, the outer sheath and elongated member are rotatably and longitudinally moved with respect to each other in a controlled and forcible manner.

FIG. 9 depicts still another embodiment of the present invention including alternative instrument engagement assembly 36 for instrument 10. Instrument engagement assembly 36 includes sheath engagement subassembly 70 positioned on the proximal end of outer sheath 11. Subassembly 70 includes hub 37 with inner sleeve 38 proximally extending therefrom. Outer sleeve 40 with thumb rest 39 is fixedly positioned longitudinally and rotatably positioned around the outer surface of inner sleeve 38 for the convenience and comfort of the surgeon when pushing the device distally. In use, the surgeon's thumb rests on and pushes against the thumb rest to urge the outer sheath distally while the surgeon's fingers gently grip and guide the hub when the pivotedly interconnected side arm is closed against the hub in the engaged position. The surgeon's other hand holds the proximal end of the elongated member.

FIG. 10 depicts yet another embodiment of the present invention including alternative instrument engagement assembly 41 for instrument 10, which includes an enhancement to instrument engagement assembly 36 of FIG. 9. Instrument engagement assembly 41 includes sheath engagement subassembly 71 positioned on the proximal end of outer sheath 11. Subassembly 71 includes hub 73 with reversed side arm 72 and inner sleeve 42 extending proximally therefrom. Outer sleeve 43 is fixedly positioned longitudinally and rotatably positioned around inner sleeve 42. Outer sleeve 43 includes a laterally extending projection with thumb rest 44 and finger pull 45 positioned distally with respect to thumb rest 44 for enhancing the convenience and comfort of the surgeon when pushing and pulling the hub of the instrument. In use, the surgeon's thumb rests on and pushes against the thumb rest while the surgeon's index finger grips and pulls the finger pull. The remaining fingers gently grip about the hub when the pivotedly interconnected arm is in the engaged position. The surgeon's other hand holds the proximal end of the elongated member.

It is to be understood that the above-described surgical cutting instrument is merely an illustrative embodiment of the principles of this invention and that other surgical cutting instruments may be devised by those skilled in the art without departing from the spirit and scope of this invention. It is contemplated that other instrument engagement assemblies may be devised for providing controlled longitudinal movement of the outer sheath and inner elongated member with respect to each other. For example, the positioning of the projections and multiple-start threads can be reversed on the outer sheath and inner elongated member. It is also contemplated that a ratchet type movement can be employed. It is further contemplated that the number of helical grooves or starts of external threads comprising the positioning portion on the elongated member can be varied to change, for example, the force or the distance traveled in one rotation of the outer sheath. It is also further contemplated that the distal, tissue affixation end of the elongated member can comprise any number of grasping apparatus such as a hook, a spike, a plurality of fingers, or forceps jaws. It is still further contemplated that well-known seals can be positioned at the proximal end of the outer sheath to prevent insufflation gas from escaping the body cavity when the inner member is withdrawn for removing tissue plugs.

What is claimed is:

1. A surgical cutting instrument comprising:

an outer sheath having a distal cutting end, a proximal end, and a passage extending longitudinally therethrough;

an elongated member at least part of which can be inserted through said passage of said outer sheath and having a distal end extendable from said distal cutting end of said outer sheath when positioned in said passage of said outer sheath, said distal end of said elongated member having a part fixable in tissue; and assembly means positioned on at least one of said outer sheath and said elongated member for rotating said outer sheath and moving said distal cutting end thereof toward said distal end of said elongated member when said distal end of said elongated member is extended from said distal cutting end of said outer sheath and retained in a fixed position with tissue affixed thereto, whereby forward and rotational movement of said outer sheath causes said distal cutting end to rotate and core tissue affixed to said distal end of said elongated member;

wherein said assembly means includes sheath engagement means positioned on said outer sheath and member engagement means positioned on said elongated member for selectively engaging each other;

wherein said sheath engagement means includes a hub attached about said proximal end of said outer sheath and having a passage communicating with said passage of said outer sheath;

wherein said member engagement means includes positioning means for controlling the position of said elongated member in said passage of said outer sheath;

wherein said sheath engagement means further includes selector means attached to said hub for selectively engaging said positioning means;

wherein said positioning means includes an intermediate portion of said elongated member having an outer surface and a helical groove in said outer surface; and wherein said selector means comprises an arm slidably attached to said hub, said arm having a slot therethrough communicating with said passage of said hub, said slot having a plurality of at least partial grooves mating with said helical groove of said proximal portion of said elongated member when said instrument engagement means is in said predetermined position.

2. A surgical cutting instrument comprising:

an outer sheath having a distal cutting end, a proximal end, and a passage extending longitudinally therethrough;

an elongated member at least part of which can be inserted through said passage of said outer sheath and having a distal end extendable from said distal cutting end of said outer sheath when positioned in said passage of said outer sheath, said distal end of said elongated member having a part fixable in tissue;

a hub attached about said proximal end of said outer sheath and having a passage communicating with said passage of said outer sheath and at least one projection positioned in said passage of said hub when in a predetermined position; and an intermediate portion of said member having an outer surface and a helical groove in said outer surface engaging said at least one projection, said at least one projection and said helical groove for rotating said outer sheath and moving said distal cutting end toward said distal end of said elongated member when said distal end of said elongated member is extended from said distal cutting end of said outer sheath and retained in a fixed position with tissue affixed thereto, whereby forward and rotational movement of said outer sheath causes said distal cutting end to rotate and core tissue affixed to said distal end of said elongated member;

wherein said hub includes a side arm pivotedly connected thereto and having said at least one projection extending laterally therefrom and into said passage of said hub when in said passage of said hub when in said predetermined position; and wherein said hub includes a sleeve fixedly positioned longitudinally and rotatably positioned around a proximal end thereof.

3. The instrument of claim 2 wherein said sleeve includes a thumb rest positioned on an outer surface of said sleeve.

4. The instrument of claim 3 wherein said thumb rest includes a finger pull.

5. A method of coring biological tissue comprising the steps of:

introducing an elongated member through a tube towards the tissue, the tube having a cutting mechanism at its distal end thereof, and the member having tissue attachment means at its distal end;

affixing the attachment means to a first tissue;

moving the cutting mechanism into the tissue with longitudinal and rotary movement relative to the first fixed tissue, whereby the first fixed tissue is cored and retained within the distal end of the tube;

simultaneously withdrawing the attachment means and the distal end of the tube from the tissue;

moving the attachment means and the tube to another site;

affixing the attachment means to a second tissue at said other site; and moving the cutting mechanism into the tissue at said other site with longitudinal and rotary movement relative to the second fixed tissue, whereby the second fixed tissue is cored and retained within the distal end of the tube distally of the first fixed tissue.

* * * * *